United States Patent [19]

Szczesuil et al.

[11] Patent Number: 5,538,583
[45] Date of Patent: Jul. 23, 1996

[54] METHOD OF MANUFACTURING A LAMINATED TEXTILE SUBSTRATE FOR A BODY HEATING OR COOLING GARMENT

[75] Inventors: Stephen P. Szczesuil, Framingham, Mass.; Rizalah Masadi, Woonsocket, R.I.

[73] Assignee: The United States of America as represented by the Secretary of the Army, Washington, D.C.

[21] Appl. No.: 436,701

[22] Filed: May 5, 1995

Related U.S. Application Data

[60] Continuation of Ser. No. 203,969, Mar. 1, 1994, abandoned, which is a division of Ser. No. 993,741, Dec. 10, 1992, Pat. No. 5,320,164.

[51] Int. Cl.⁶ ............................................. B32B 7/14
[52] U.S. Cl. ........................ 156/291; 156/324.4; 2/2
[58] Field of Search ........................... 165/46; 156/291, 156/324.4; 2/2

[56] References Cited

U.S. PATENT DOCUMENTS

| | | |
|---|---|---|
| 2,652,824 | 9/1953 | Hopp . |
| 3,251,727 | 5/1966 | Reynolds et al. ............ 156/291 |
| 3,383,263 | 5/1968 | Storti ............................ 156/235 |
| 3,419,702 | 12/1968 | Piel . |
| 3,425,486 | 2/1969 | Burton et al. . |
| 3,452,812 | 7/1969 | Betts . |
| 3,598,689 | 8/1971 | Feffer et al. ................... 156/291 |
| 3,717,528 | 2/1973 | Peerman et al. ............ 156/324.4 |
| 4,114,620 | 9/1978 | Moore et al. . |
| 4,677,970 | 7/1987 | Green et al. . |
| 4,691,762 | 9/1987 | Elkins et al. . |
| 4,718,429 | 1/1988 | Smidt . |
| 4,998,415 | 3/1991 | Larsen . |
| 5,005,611 | 4/1991 | Hecker ........................... 140/147 |
| 5,062,424 | 11/1991 | Hooker . |

OTHER PUBLICATIONS

"Exotemp CD2 Cooling System" brochure, Exotemp Ltd., 320 Boundary Road, Unit 130, Pembroke, Ontario (publication date unknown).

"Care and Use of Exotemp Heat Transfer Garment" brochure, Exotemp Ltd., 320 Boundary Road, R.R. #4, Pembroke, Ontario, dated Oct. 1991.

"The Model17 Cpmfort Vest" brochure, ILC Dover, Inc., P.O. Box 266, Frederica, Delaware 19946 (publication date unknown).

*Primary Examiner*—Jeff H. Aftergut
*Assistant Examiner*—Richard Crispino
*Attorney, Agent, or Firm*—John H. Lamming; Vincent J. Ranucci

[57] ABSTRACT

A method for making body heating/cooling garment which utilizes fluid-carrying tubes and provides both air and vapor permeability to promote convective heat transfer while also providing conductive heat transfer.

8 Claims, 5 Drawing Sheets

METHOD OF MANUFACTURING A LAMINATED TEXTILE SUBSTRATE FOR A BODY HEATING OR COOLING GARMENT

STATEMENT OF GOVERNMENT INTEREST

The invention described herein may be manufactured, used and licensed by or for the Government for Governmental purposes without the payment to us of any royalties thereon.

This application is a continuation of patent application Ser. No. 08/203,969 filed Mar. 1, 1994, now abandoned, which was a division of patent application Ser. No. 07/993,741, filed Dec. 10, 1992 now U.S. Pat. No. 5,320,164.

FIELD OF INVENTION

This invention relates to a method for fabricating body heating and cooling garments which utilize fluid-carrying tubes for heat transfer, and more particularly to a body heating/cooling garment that provides both air and vapor permeability to promote convective heat transfer while providing conductive heat transfer.

BACKGROUND OF THE INVENTION

For some time it has been a critical requirement for both soldiers and for those operating in extreme temperature environments, especially in the Arctic and in the desert, that a garment be provided which is both air and vapor permeable while at the same time having synthetic tubing carrying cooling or heating fluids in which close body contact is made with the tubing.

Typically, a heating/cooling garment, such as a vest, is made in which tubing is attached to a liner, with the liner then attached to fabric which forms the outer portion of the garment. While a wide variety of such garments exist, garments for this purpose are desirably stretchable and flexible to conform to the body of the individual, not only to provide mobility for arms and legs, but also to hold the cooling tubes closer to the body for more efficient heat transfer to the heating or cooling fluid. Additionally, flexibility produces less damage to the tubing during the flexure of the garment, with the garment being less susceptible to being torn when the material is flexible. Moreover, there is a requirement for lightweight construction, launderability, and dry cleanability. Additionally, since pressures within the tubing can reach 100 psi, the mating of the tubing to its substrate must be fluid pressure insensitive.

In the past, such a garment has involved the sewing of tubing to a substrate or liner which is porous enough to provide both for internal vapors to escape as well as to provide for air permeability. However, a major problem with sewn tubing is a problem called needleholing, in which every inch of the tubing is sewn to the porous substrate. Not only is there a potential problem in terms of pinhole puncturing of the tubing during the sewing process, the threads themselves provide a major irritant when these tubes are pressed into contact with the body. Additionally, since a T-shirt made in this manner can take as long as one day to manufacture and another day to test, the sewing method is intolerably slow and expensive, with registration problems of the tubing with a predetermined pattern making automatic sewing all but impossible.

Another reason that stitching is avoided is in so-called chemical protective clothing. Here, stitching tubing to any substrate for use in this application will result in needle holes, the size of which will permit unwanted chemicals to transit from one side of the garment to the other. Sewn tubing type garments are exemplified by Exotemp Ltd. heat transfer garments.

In order to provide an alternative to the sewn-in tubing, heating/cooling garments have been made with a bladder sealed at its edges, with the cooling fluid being contained within the bladder. However, while bladder-type garments do in fact conduct heat away from the body or conduct heat to the body, due to the two-coated fabrics which are joined together by heat, the resulting garment is non-breathable, non-stretchable and non-flexible. Additionally, there is a flexibility problem because of the large volume of liquid which is captured in the garment. Also, there is only one method of removing heat, e.g., conduction, since a bladder-type garment poses an impermeable barrier against natural sweating. Such a cooling garment thus completely eliminates the possibility of evaporative or convective cooling. Further, the edges of the bladder can come apart when subjected to pressures higher than 30 psi. Bladder type garments are exemplified by COOLVEST Model 17 manufactured by ILC DOVER.

Bladder type garments aside, methods other than sewing have been used to attach tubing to a liner or substrate. One such method involves brushing or rolling adhesives onto liners.

While brushed on or rolled on adhesives have been used in an attempt to adhere tubing to liners, the result is that all lining porosity is destroyed when the adhesive is massively applied across the substrate.

There is also a technique for adhesively taping the tubing to a liner, with adhesive tape contacting the liner to either side of the tube along its length. This system is exceedingly difficult to implement due to the fact that when the tubing is formed around small radius corners, the overlying strip of tape has to be notched to go around the corners. Also, it will be appreciated that the tape retards stretchability and permeability, adds unwanted stiffness to the garment and does not result in secure fastening of the tubing to the liner.

In general, heating or cooling garments are exemplified by U.S. Pat. Nos. 3,451,812; 3,425,486; 3,419,702; 4,691,762; 4,718,429; and 4,998,415. Other types of systems for body heating and cooling are illustrated in U.S. Pat. Nos. 4,114,620 and 5,062,424.

None of the above patents describe the utilization of a substrate or liner which is both air permeable and vapor permeable to which tubing is attached using fusible fabrics.

In summary, it is important to provide a garment that does not restrict the evaporative process in that it does not restrict the natural evaporation process of the human body, thereby preventing heat stress. It is therefore important that the garment not trap vapor as is the case with both bladder-type garments and those garments which have an excessive amount of adhesive blocking the naturally occurring pores in the liner. While some of the sewn in tubing garments provide for many of the above features, needleholing due to stitching and exhorbitant amounts of time spent in making the garment, as well as testing it after manufacture, preclude large scale usage. The sewn method precludes use in chemical protective uniform applications. Also, the sewn tubing method can be uncomfortable to the wearer.

SUMMARY OF THE INVENTION

In order to alleviate the problems due to stitching of tubing to a liner of a garment, in the subject invention, tubing is fused by fusible dots on a fusible fabric both to the fusible fabric end to an overlying liner. Both the fusible fabric and the liner have air and vapor permeability so that the final product is likewise air and vapor permeable. In one embodiment, tubing is first adhesively attached to an air permeable and vapor permeable fusible fabric substrate having an adhesive dot pattern on the surface to which the tubing is to be adhered, with the fabric being attached via the dots in a fusing process involving heat and pressure. The adhesive dots on the fusible fabric are melted through heat and under pressure so that they attach to the tubing, thereby forming a unitized bicomponent construction. The bicomponent tubing and fusible fabric construction is then placed, tubing down, over an air permeable and vapor permeable fusible or non-fusible pattern piece which may be in the form of a textile liner material, not necessarily of the same type as the fusible fabric. The composite is then refused under heat and pressure. This process remelts the fusible dots from the fusible fabric material which attach themselves to the liner and consequently envelope the tubing to serve as an interlining. The completed tricomponent construction, which forms the body of the garment as a finished product, remains air and vapor permeable, stretchable and wash resistant.

In another embodiment, tubing is first temporarily adhered to a non-fusible pattern piece. To accomplish this, tubing, such as silicone, teflon, or other nonstick type is coated with a self-stick adhesive. The coated tubing is then placed in a desired configuration on top of the fusible or non-fusible air and vapor permeable pattern piece, with the tubing and pattern piece forming a bicomponent construction. An air and vapor permeable fusible fabric substrate is then placed over the bicomponent construction, which is placed under heat and pressure. As above, this process melts the fusible fabric dots from the top fusible fabric material, with the dots attaching themselves to the pattern piece and consequently enveloping the tubing to serve as an interlining. Again, the completed tricomponent construction which forms the finished product, remains air and vapor permeable, stretchable and wash resistant.

More specifically, a self-stick adhesive is first applied to the outside of the tubing. The adhesive is extremely aggressive, non-toxic and non-hazardous to general health. Subsequently, the tubing is then manually lightly applied to the flat pattern textile product or pattern piece in a desired tubing pattern, with the pattern piece being sufficiently porous to provide the above-mentioned breathability. This may be accomplished by overlying the pattern piece with a stencil-like mask having serpentine slots to locate the tubing.

When the shape of the tubing is confirmed to be correct, the tubing is then pressed hard for positive contact, with the shape being easily changed by moving the tubing without any adhesive residue problems. When firmly pressed into the pattern piece, a lightweight fusible fabric, using any given substrate type (woven, knitted or non-woven) with a polyamide, polyester, polyethylene, polyvinyl chloride (PVC) or any combination thereof fusible fabric dot adhesive thereon, is placed over the pattern piece and is fused into place. The fusible fabric functions to permanently lock in the tubing, to line the end item, and to gently deflect the harshness of the tubing and effective cold or heat from direct contact with the skin. In one embodiment, the material for the fusible fabric is a tricot knit, manufactured by HTC-Handler Co., whereas the dot pattern adhesive is available from HTC-Handler as Transweb model polyamide adhesive. Fusible fabrics also include Pellon[R] manufactured by the Freudenberg Corporation of Chelmsford, Mass.

As will be appreciated, the material to become a fusible fabric is first coated with a pattern of heat and pressure activated adhesive dots which are either randomly generated or which have a predetermined pattern, with the dot pattern being carried by a calendar roll or like device. The adhesive dots may be either polyamides, polyester, polyethylene, PVC or any combination thereof. The dot size and pattern is arranged so that no significant occlusion of the open portions of the substrate occurs. Also, applying adhesive dots to an open substrate by initial fusing results in only the fibers or strands being coated, and not the spaces between the fibers or strands. Moreover, because of the dot pattern there are no registration problems when laying down the tubing. Note, the final garment will have almost the same air and vapor permeability as that associated with the original substrate because the patterned adhesive need not be exceptionally dense.

By fabricating a fusible fabric in this manner, brushing and rolling or coating of substrates is completely eliminated, and significant stretchability and flexibility is achieved because the dot pattern is not sufficiently dense to either close up the holes within the liner or to add significant stiffness or weight to the final garment. The construction is lightweight, and is launderable, and in fact there is more efficient heat transfer either to or from the body because of the flexibility of the garment and the fact that the tubing when fused to the liner goes to an oval configuration with more surface area in contact with the body. Moreover, it will be appreciated that the adhesive utilized does not take any significant load, which reduces stress cracking that is associated with other type adhesive systems.

Finally, the entire system is insensitive to the pressure of the fluids within the tubing, unlike the bladder-type garments in which the sealed edges fail when subjected to high fluidic pressures. Additionally, there is no skin irritation associated with sewing, and the needleholing problem associated with sewing is completely eliminated.

What is therefore provided is a system in which garments can be given the breathability necessary for hot and cold climate use while providing sufficient flexibility and stretchability.

The subject system also obviates the need for coated plastics which are undesirable because they are not elastic, are non-flexible and are most importantly, non-permeable.

While the Subject Invention is described in terms of a liner for a pattern piece which forms the exterior of a garment, the system includes the use of the tubing fused to an air/vapor permeable substrate used by itself or with any other garment component.

BRIEF DESCRIPTION OF THE DRAWINGS

These and other features of the Subject Invention will be better understood taken in conjunction with the Detailed Description in conjunction with the Drawings of which.

DETAILED DESCRIPTION

Figure 1:
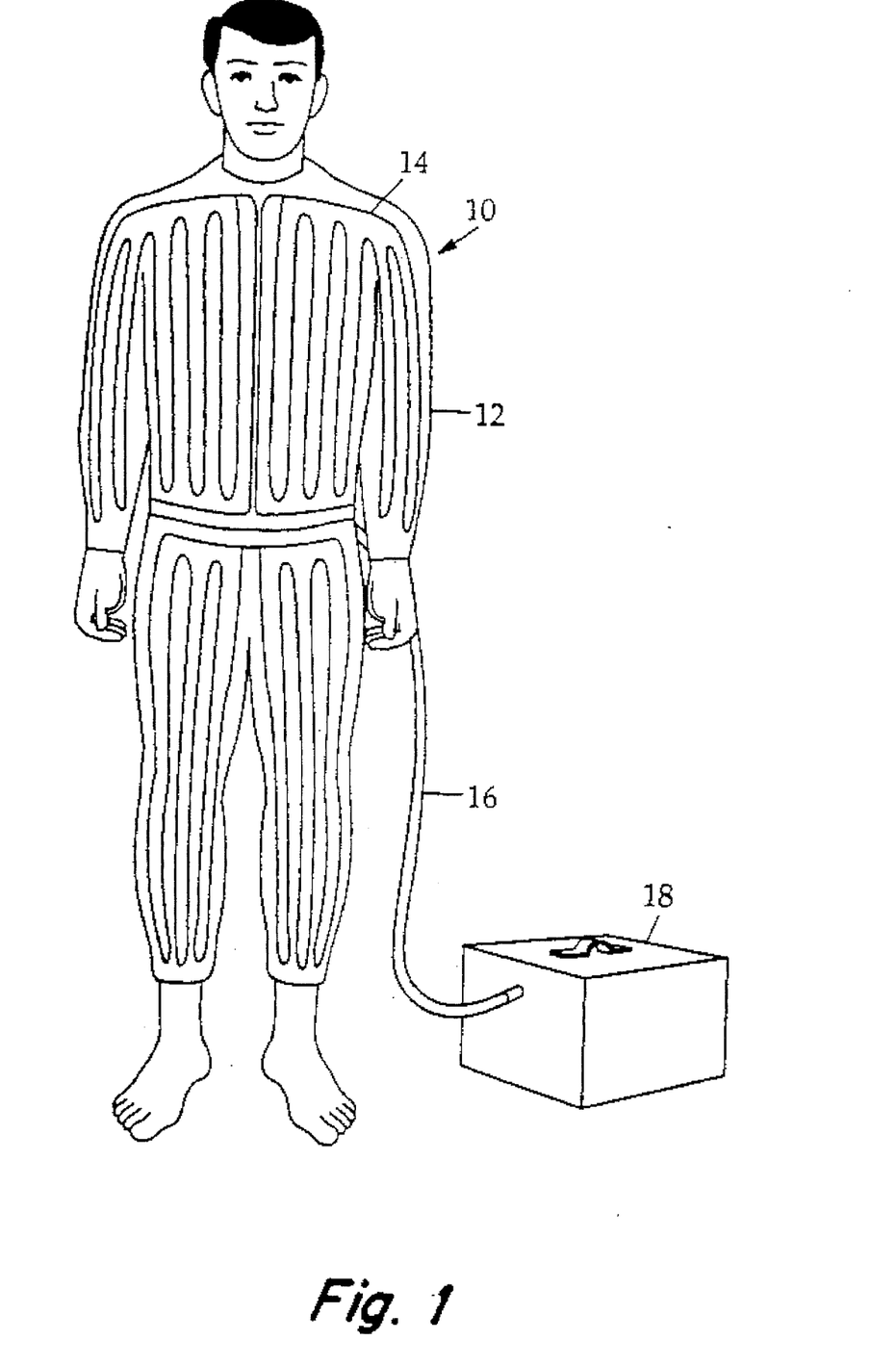
FIG. 1 is a diagrammatic representation of a heating or cooling suit or garment having tubes through which heating or cooling liquid is pumped.

Referring now to FIG. 1, an individual 10 may be provided with a garment or suit 12 having heating or cooling tubing 14 dispersed thereacross, with the tubing being supplied with heating or cooling fluids via an umbilical connection line 16 from a heating/cooling unit 18. As has been mentioned hereinbefore, it is essential that such a garment be extremely flexible, durable, and most importantly, be both air and vapor permeable to permit cooling via not only the conduction of the tubing adjacent to the individual's body, but also by the escape of vapor from the body to ambient, which in essence is cooling via convection.

Figure 2:
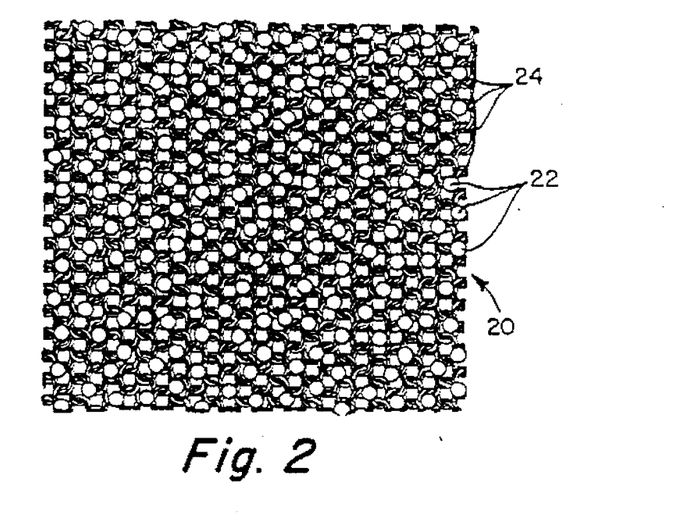
FIG. 2 is a top view of an air/vapor permeable fusible fabric illustrating an adhesive dot pattern across the surface of the fusible fabric in which the adhesive dots are heat and pressure activated and, as illustrated, are randomly placed so as to not exceed a dot density that significantly affects the porosity of the fusible fabric.

In order to achieve such a flexible, durable and lightweight garment with the required properties, in one embodiment, and referring now to FIG. 2, a fusible fabric 20 is in general an open weave or open lattice structure which may or may not be woven but which provides in and of itself for the air permeability and vapor permeability or required. In general porosity is measured by the amount of cubic feet of air per minute per square foot that can transit from one side of the garment to the other. It will be appreciated that a range of, for instance, between four cubic feet per minute per square foot for tents and the like, to about 50 cubic feet per minute per square foot for everyday garments is standard; whereas for uniform garments and for some dress apparel and knit apparel, the air permeability can be as much as 300 cubic feet per minute per square foot. It will be appreciated that bladder type garments have a zero air and vapor permeabilities.

Note, that it is possible to have a semi-permeable fabric, in which there is low or zero air permeability, in which there is in fact vapor permeability. This situation is like the physics behind a semi-permeable membrane. Poor air permeability is not preferred for use in such semi-permeable fabrics for heating/cooling garments.

Vapor permeability is measured through the utilization of a heated mannequin which is wet. The vapor transmission through the fabrics is then measured, for which there are American Society of Testing Materials (ASTM) procedures, such as discussed in ASTM Designation E96-80 which describes a standard test method for water vapor transmission of materials. ASTM Designation D737-75 describes the standard test method for air permeability of textile fabrics.

In general, while acceptable air permeability is that which exceeds 50 cubic feet per second per square foot, acceptable vapor permeability is defined as follows: Minimum acceptable vapor permeability is 600 grams per square meter per 24 hours. Note, the range of acceptable vapor permeability for impermeable fabrics as 0–50 g/m$^2$/24 hrs; semi-permeable fabrics is 600–1000 g/m$^2$/24 hrs; and permeable fabrics is 700–1500 g/m$^2$/24 hrs.

With respect to the fusible fabrics themselves, military specifications classify fusible cloth as Type I - plain weave substrate, Type II - twill weave substrate, Type III - weft inserted knit substrate, Type IV - tricot knit substrate, Type V - thermal bonded non-woven substrate, Type VI - saturate bonded non-woven substrate, Type VII - spun bonded non-woven substrate, Type VIII - spun lace non-woven substrate, and Type IX - open net web substrate. Another type of fusible cloth which is useful in this invention is circular knit cloth.

With respect to the types of adhesives used with the fusible fabric, note that Class 1 includes polyamid adhesives, whereas Class 2 includes polyester adhesives, Class 3 - polyethelene high density adhesives, Class 4 - polyvinyl chloride/polyvinyl acetate adhesives and Class 5 - polyvinyl acetate copolymer (double-sided) adhesives. The above is reflected in military specification standard MIL-C-44296A.

With respect to the adhesive applications for this item, the dots are uniformly distributed, powder dot, paste dot, hot melt dot, bicomponent dot or sintered fusible adhesive dot, all evenly applied to one side in accordance with standard commercial practice, with the powder dot adhesive to be transferred from a hopper bed to an engraved, and heat treated roll, such that a predetermined number of dots per square inch and particle size are deposited onto the fusible substrate.

With respect to paste dots, the adhesive is dispersed and transferred from a circular perforated screen with a predetermined number of dots per square inch onto the fusible substrate. Another process includes calendering methods using finely engraved rolls.

With respect to hot melt dots, the adhesive is in the form of polymer chips melted and transferred from an engraving roll of a predetermined dot per square inch pattern onto a substrate forming the fusible fabric.

With respect to bicomponent dots the adhesive is a blend of two polymers of different melting properties transferred onto the substrate using a predetermined dot per square inch pattern.

With respect to sintered adhesives, they are randomly scattered in equal amounts on the substrate which is in turn heated to melt-fuse the adhesive onto the substrate forming the fusible fabric.

With respect to spun-fused adhesives, these adhesives are applied as polymer chips melted and extruded in a web formation either in unsupported configuration or onto one or both sides of a substrate. The number of dots per square inch in one embodiment is 175 for a tricot knit substrate of nylon.

The substrate porosity can be defined as air permeability and is typically between 50–300 cubic feet/second/square foot.

This having been said, fusible fabric 20 of FIG. 2 includes a number of patterned dots 22 which adhere to the intersections between the woven strands 24 which, in one embodiment, adhere only to the strands and do not occupy the spaces between the strands. Thus the original porosity of the fusible fabric is maintained by virtue of an adhesive dot pattern which does not significantly occlude the spaces between the warp and fill or inter-lattice spaces.

Figure 3:
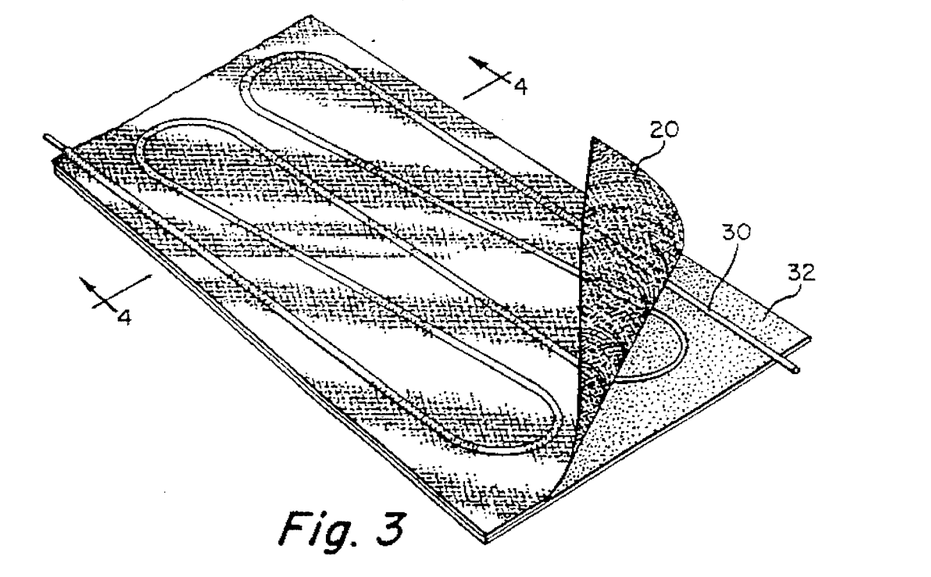
FIG. 3 is a diagrammatic illustration of a section of a pattern piece provided with a heating/cooling tube which is sandwiched between the pattern piece and the fusible fabric.

Referring now to FIG. 3, fusible fabric 20 is shown overlying a serpentine tube structure 30 which is placed on a pattern piece 32 (fusible or non-fusible) in a desired pattern. When the sandwiched structure involving the pattern piece, the tube and fusible fabric is sealed one to another with the application of heat and pressure, for instance 300° F. and 40 psi, a final structure shown in FIG. 4 includes tubing 30 sandwiched between fusible fabric 20 and pattern piece 32. It will be appreciated that the fusible fabric is adhered not only to the tubing itself but also to the pattern piece surrounding the tubing such that the tubing is captured in the laminated sandwich-type structure.

Figure 4:
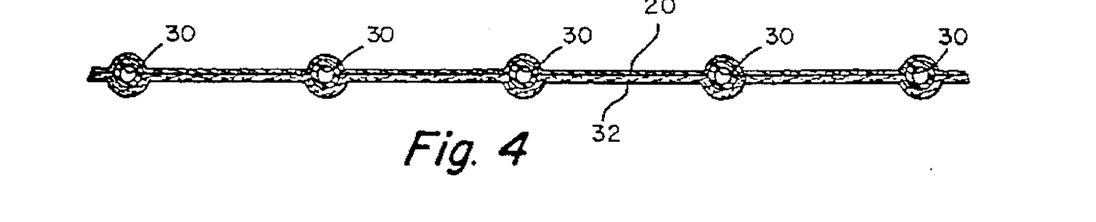
FIG. 4 is a cross-sectional diagram of the sandwich structure of FIG. 3 after the lamination process illustrating the adherence of the fusible fabric not only to the tubing but to adjacent portions of the underlying pattern piece.

It will be appreciated that the fusible fabric with the adhesive dots thereon and the pattern piece determine the ultimate air/vapor porosity for the garment, with the laminated structure providing in one embodiment a garment liner, and in another embodiment, being utilized in and of itself as a garment for the providing of the heating and cooling function.

Figure 5A:
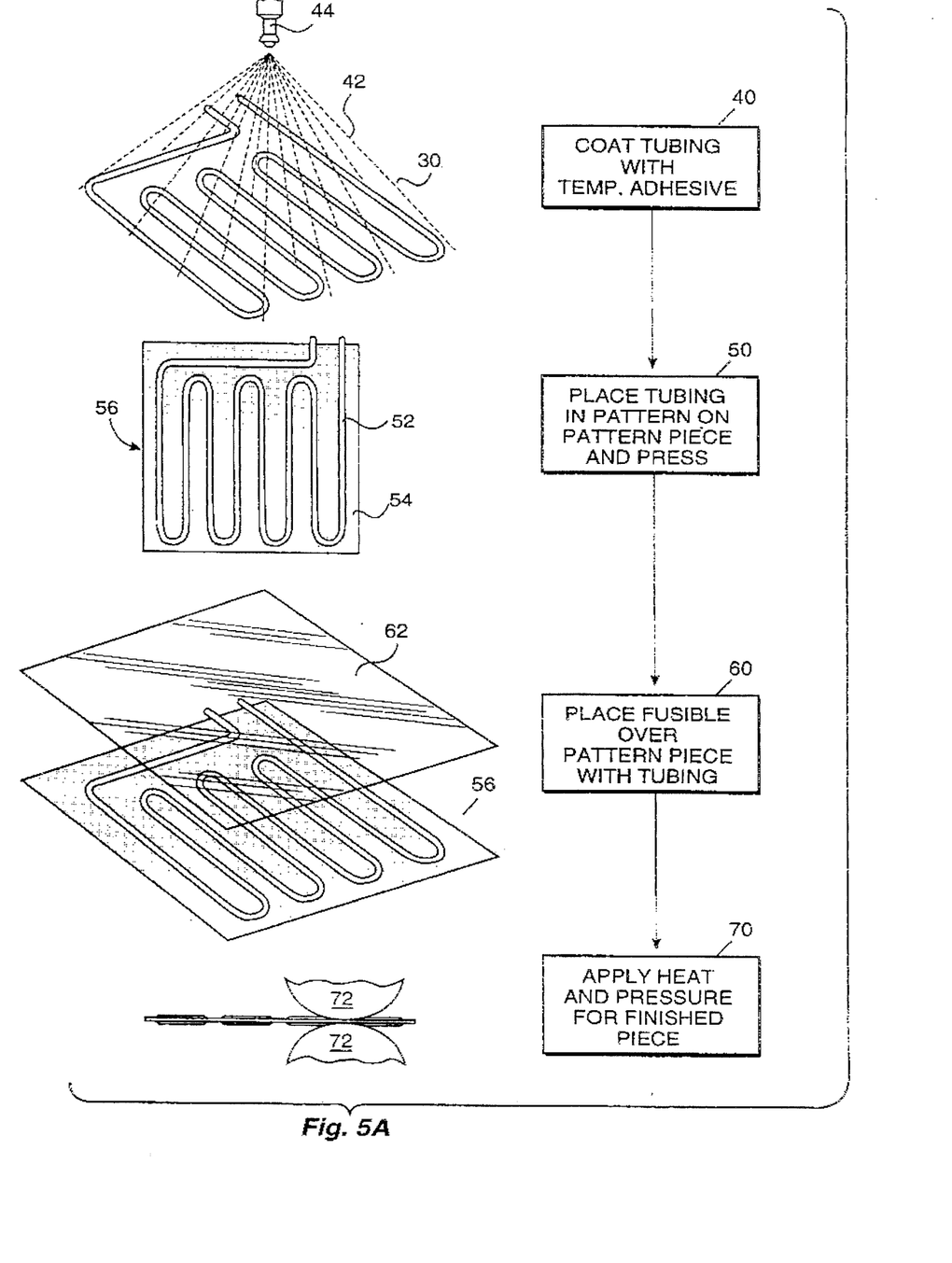
FIG. 5A is a process flow chart and accompanying diagrams illustrating one embodiment of a method for adhering heating/cooling tubing within a laminated structure.

Referring now to FIG. 5A, in one embodiment, the steps in preparing the laminated product include, as illustrated at 40, the coating of tubing 30 with a temporary adhesive 42 from a spray gun or nozzle 44. Tubing 30 may be supported by a supporting pattern board (not shown) in this figure. With the tubing so coated, the tubing is placed, as illustrated at 50, in a pattern illustrated at 52 on top of a pattern piece 54 and is pressed into place when the particular tubing pattern is correct. Thereafter as illustrated at 60 a fusible fabric 62 is placed over the resulting structure 56, and as illustrated at 70, heat and pressure are applied to the sandwich structure by heated rollers 72 so as to produce the final product with the tubing laminated between a pattern piece and a fusible fabric.

Figure 5B:
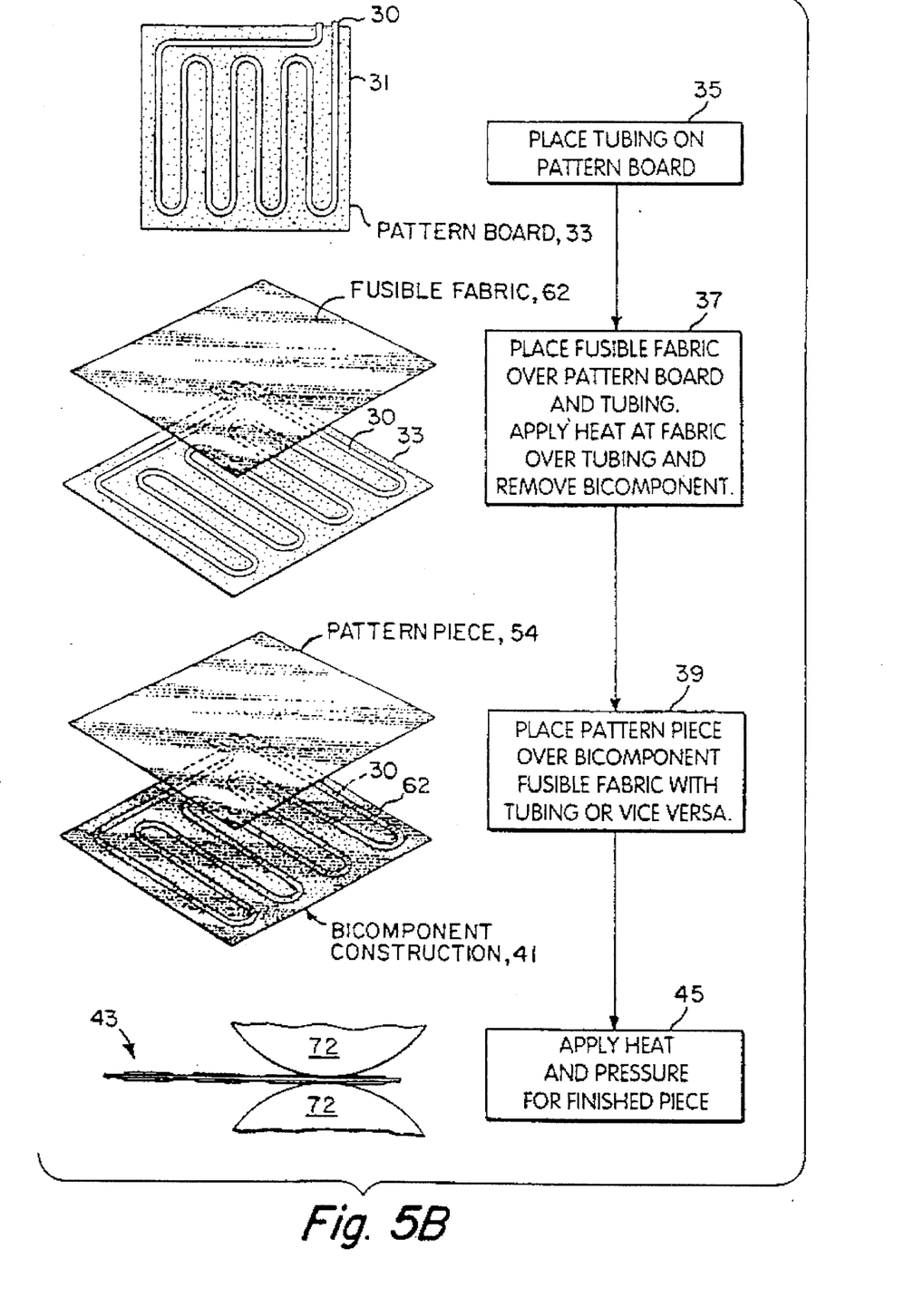
FIG. 5B is a process flow chart and accompanying figures illustrating a preferred method for adhering heating/cooling tubing within a laminated structure, in which an initial adhesive spray is not required; and, FIG. 6 is a diagrammatic illustration of a tubing pattern which may be used with the Subject Invention in which sections of the tubing are fed in parallel with oversized diameter feed tubing and return tubing, whereas the heating/cooling tubing is of a reduced diameter.

Referring now to FIG. 5B, in an alternative and preferred embodiment, tubing 30 is placed within channels 31 in a pattern board 33 as indicated at 35, with the channel in the pattern board being configured to a predetermined tubing layout for the particular pattern piece to be provided with tubing. Thereafter, a fusible fabric 62 is placed over the pattern board and the tubing, with heat and pressure being applied as illustrated at 37 to adhere the tubing to the fusible fabric. After the tubing is fused via the melting of the adhesive dots to the underneath side of the fusible fabric, the pattern board is removed and as illustrated at 39 and a pattern piece 54 is applied over the bicomponent construction or structure 41 formed in step 37. The resulting structure 43 is passed through heated rollers 72 to marry the pattern piece to the bicomponent construction to provide a finished tricomponent finished piece as illustrated at 45 through the application of pressure and heat. In this embodiment, there is no initial adhesive coating applied to tack the tubing in place either to a pattern piece or to a fusible fabric.

In either of the FIGS. 5A or 5B embodiments, the result is a tricomponent finished piece which is both air and vapor permeable and which has exceptional flexibility and durability.

This method of manufacturing the subject garment or substrate with a heating/cooling tubing adhered thereto obviates many of the problems of the prior art and provides a stretchable, flexible, air permeable, vapor permeable and durable garment or material having the required porosity, at a fraction of the cost of sewn tubing and at a fraction of the weight and cost of bladder type components.

Figure 6:
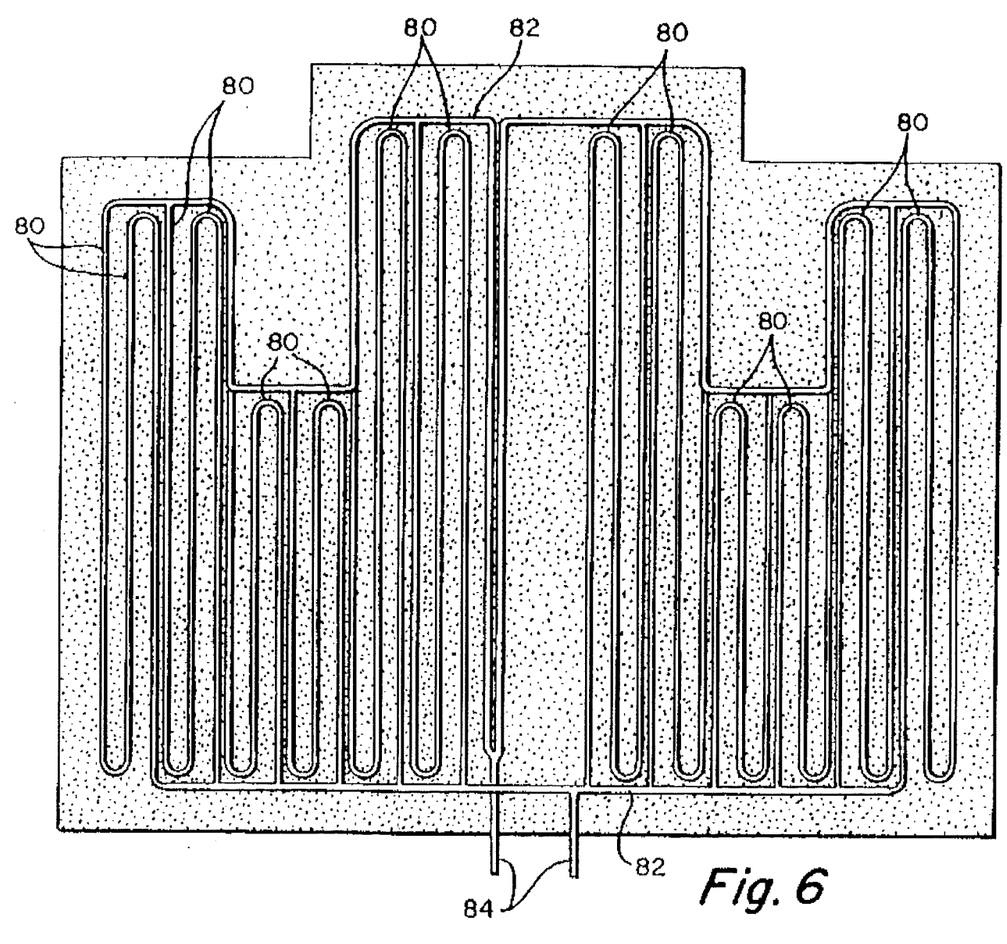

The particular pattern for the tubing is dictated by the application to which the tubing is to be placed. As illustrated in FIG. 6, heating and cooling loops 80 may be fed in parallel by larger diameter feed tubing manifold 82 which feeds the left hand and the right hand heating/cooling tubing sections, with all of the heating/cooling tubing of each section being fed in parallel. It is a feature of this design that three different sizes of tubing are utilized, one for the feed and the return, here illustrated by tubing 84, another 82 for transition of flow and another 80 for the heating/cooling tubing itself. Rather than having a serial feed with the corresponding pressure drop across the entire system, the subject parallel fed heating/cooling tubing arrangement reduces the amount of power necessary for the entire process while at the same time reducing the internal pressures and the pressurization equipment necessary in providing the fluid to the heating/cooling garment.

The different sizes of tubing can be utilized to balance the pressures within the garment, with the enlarged diameter feeding and return tubing making it practical to adjust the internal pressures within the garment and, inter alia, to improve or even tailor the heating and cooling on a region by region basis.

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. A method of manufacturing a tricomponent laminated textile substrate for a body heating or cooling garment which permits conductive and convective heat transfer, air and vapor permeability, flexibility, stretchability, and wash resistance, with tubing having feed and return means capable of being attached by an umbilical connection to means external to the textile substrate for providing heating or cooling fluids, temporary adhesive means for application to the tubing, a fabric pattern piece including fibers and spaces between the fibers and having air and vapor permeability and a tube pattern, and a fusible fabric piece also including fibers and spaces between the fibers and also having air and vapor permeability and heat and pressure activated fusible fabric dot adhesive means selected from the group consisting of polyamide, polyester, polyethylene, polyvinyl chloride, and any combination thereof, in the form of a pattern of adhesive dots sized and arranged so that no significant occlusion of the open portions of the fabric pattern piece and the fusible fabric piece occurs after application of heat and pressure thereto, comprising the steps of:

(a) coating the tubing with temporary adhesive means;

(b) placing the tubing thus coated onto the fabric pattern piece in accordance with the tube pattern;

(c) pressing the tubing into place so that it is held in place by the temporary adhesive means to form a unitary bicomponent structure in which the adhesive means substantially touch only the fibers and does not spread into the spaces between fibers;

(d) placing the fusible fabric piece over the bicomponent structure thus formed so that the tubing is enveloped between the fabric pattern piece and the fusible fabric piece; and (e) applying heat and pressure to melt the temporary adhesive means applied to the tubing to fuse the tubing to the fabric pattern piece and to melt said heat and pressure activated fusible fabric dot adhesive means of the fusible fabric piece to fuse the tubing to the fusible fabric piece and to fuse the fusible fabric piece to the fabric pattern piece so that the temporary adhesive means and the heat and pressure activated fusible fabric dot adhesive means substantially touch only the fibers of the fabric pattern piece and the fusible fabric piece and not the spaces between fibers thereof to bond said fabric pieces without significant occlusion of the spaces between the fibers of the fabric pattern piece and the fusible fabric piece, substantially maintaining the original air and vapor permeability of the fabric pattern piece and the fusible fabric piece to form a fused unitary tricomponent laminated textile substrate comprised of the fabric pattern piece, the tubing and the fusible fabric piece, wherein the tubing is enveloped between the fabric pattern piece and the fusible fabric piece, said tricomponent laminated textile substrate thus formed having the desired properties of thermal conductance and convection, air permeability of between about 50 and 300 cubic feet per minute per square foot and vapor permeability of not less than about 600 grams per square meter per 24 hours, flexibility, stretchability, and wash resistance.

2. The method of claim 1 wherein the fabric pattern piece is supported by a tubing channel pattern board.

3. A method of manufacturing a tricomponent laminated textile substrate for a body heating or cooling garment which permits conductive and convective heat transfer, air and vapor permeability, flexibility, stretchability, and wash resistance, with tubing having feed and return means capable of being attached by an umbilical connection to means external to the textile substrate for providing heating or cooling fluids, a first fabric piece including fibers and spaces between the fibers and having air and vapor permeability comprised of a fusible fabric material having heat and pressure activated fusible fabric dot adhesive means selected from the group consisting of polyamide, polyester, polyethylene, polyvinyl chloride, and any combination thereof, in the form of a pattern of adhesive dots, and a second fabric piece also including fibers and spaces between the fibers and also having air and vapor permeability, said adhesive dots of the first fabric piece being sized and arranged so that no significant occlusion of the spaces between fibers of the first and second fabric pieces occurs after application of heat and pressure thereto, comprising the steps of:

(a) placing the tubing on a tubing channel pattern board having a tubing channel pattern formed by channel indentations in the board, so that the tubing lies within the tubing channel pattern;

(b) placing the first fabric piece over the tubing lying within the channel pattern;

(c) applying heat to the first fabric piece to fuse the tubing and the first fabric piece to form a fused unitary bicomponent substrate;

(d) removing the bicomponent substrate thus formed from the pattern board;

(e) placing the second fabric piece on the bicomponent substrate so that the tubing is enveloped between the first fabric piece and the second fabric piece; and (f) applying heat and pressure to melt and disperse the adhesive means of the fusible fabric material without significant occlusion of the spaces between the fibers of the first and second fabric pieces substantially to maintain the original air and vapor permeability of said first and second fabric pieces, fusing the unitary bicomponent substrate to the second fabric piece to form a fused unitary tricomponent laminated textile substrate comprising the first fabric piece, the tubing and the second fabric piece, wherein the tubing is enveloped between the first and second fabric pieces, to form a tricomponent laminated textile substrate having the desired properties of thermal conductance and convection, air permeability of between about 50 and 300 cubic feet per minute per square foot and vapor permeability of not less than about 600 grams per square meter per 24 hours, flexibility, stretchability, and wash resistance.

4. The method of claim 3 wherein the second fabric piece is comprised of a fusible fabric material.

5. The method of claim 4 wherein the pattern board has tubing channels for: heating or cooling tubing, tubing manifolds having larger diameter than the heating or cooling tubing, and feed and return means having larger diameter than the tubing manifolds.

6. The method of claim 5 wherein the tubing channels of the tubing channel pattern board form a tubing pattern array conforming to the desired pattern for the tubing of the tricomponent laminated textile substrate being formed containing at least one heating or cooling section, each section comprising a multiplicity of looped heating or cooling tubing forming a substantially parallel array of tubing enveloped by tubing manifolds looped in a substantially parallel array and having junctions between the tubing manifolds and the heating or cooling tubing to permit the passage of fluid freely among them, the tubing manifolds connecting separate heating or cooling sections; and in addition thereto feed and return means, each connected at one junction to the tubing manifold for connection to an external source of heating or cooling fluid; the feed and return means thus providing a continuous flow of heating or cooling fluid to the manifold tubing which feeds the heating or cooling tubing of each section of tubing in the tricomponent laminated textile substrate in parallel, and further providing a substantially uniform fluid pressure throughout the tubing of the textile substrate.

7. The method of claim 3 wherein the pattern board has tubing channels for: heating or cooling tubing, tubing manifolds having larger diameter than the heating or cooling tubing, and feed and return means having larger diameter than the tubing manifolds.

8. The method of claim 7 wherein the tubing channels of the tubing channel pattern board form a tubing pattern array conforming to the desired pattern for the tubing of the tricomponent laminated textile substrate being formed containing at least one heating or cooling section, each comprising a multiplicity of looped heating or cooling tubing forming a substantially parallel array of tubing enveloped by tubing manifolds looped in a substantially parallel array and having junctions between the tubing manifolds and the heating or cooling tubing to permit the passage of fluid freely among them, the tubing manifolds connecting separate heating or cooling sections; and in addition thereto feed and return means, each connected at one junction to the tubing manifold for connection to an external source of heating or cooling fluid; the feed and return means thus providing a continuous flow of heating or cooling fluid to the manifold tubing which feeds the heating or cooling tubing of each section of tubing in the tricomponent laminated textile substrate in parallel, and further providing a substantially uniform fluid pressure throughout the tubing of the textile substrate.

* * * * *